(12) United States Patent
Rossi et al.

(10) Patent No.: US 6,361,513 B1
(45) Date of Patent: Mar. 26, 2002

(54) ARTICULATED ROD FOR A HIP SUPPORT

(75) Inventors: Paolo Rossi, Stansstad, NW (CH); Aldo Bernareggi, Milan (IT)

(73) Assignee: Orthoscharer & Co. di Paolo Rossi & Co., Stansstad (CH)

( * ) Notice: Subject to any disclaimer, the term of this patent is extended or adjusted under 35 U.S.C. 154(b) by 0 days.

(21) Appl. No.: 09/612,687

(22) Filed: Jul. 10, 2000

(30) Foreign Application Priority Data

Jul. 13, 1999 (IT) ........................................ 99A 001537

(51) Int. Cl.[7] .................................................. A61F 5/00
(52) U.S. Cl. .......................................... 602/16; 602/23
(58) Field of Search .............................. 602/5, 16, 19; 128/846, 869, 882

(56) References Cited

U.S. PATENT DOCUMENTS

| | | | | |
|---|---|---|---|---|
| 2,545,843 A | * | 3/1951 | Cohen | 602/16 |
| 4,481,941 A | * | 11/1984 | Rolfes | 602/16 |
| 4,905,678 A | | 3/1990 | Cumins | |
| 5,421,810 A | * | 6/1995 | Davis | |
| 5,538,499 A | | 7/1996 | Schwenn | |
| 5,683,353 A | * | 11/1997 | Hamersly | 602/16 |
| 5,772,619 A | | 6/1998 | Corbett | |
| 5,860,943 A | | 1/1999 | Bloedau | |
| 6,203,511 B1 | * | 3/2001 | Johnson | 602/16 |

* cited by examiner

*Primary Examiner*—Michael A. Brown
(74) *Attorney, Agent, or Firm*—Hedman & Costigan, P.C.

(57) ABSTRACT

An articulated rod (14) for a hip support (11) comprises a first element (22) designed to be associated to a pelvis harness (12), and a second element (28) designed to be associated to a thigh harness (16). The first element (22) and second element (28) are joined together by means of a hinge (30). The hinge (30) comprises a first plate (34) which is fixed to the first element (22) and has a face set against a corresponding face of an articulation plate (50), the first plate (34) and the articulation plate (50) being joined by means of a closing element (40) inserted in aligned through holes of the first plate (34) and of the articulation plate (50). In addition, the first plate (34) has holes (42) which are set along one portion of its own periphery and in which adjustment elements (44) can be inserted. The said adjustment elements (44) are designed to limit rotation of said articulation plate (50) with respect to the first plate (34).

8 Claims, 3 Drawing Sheets

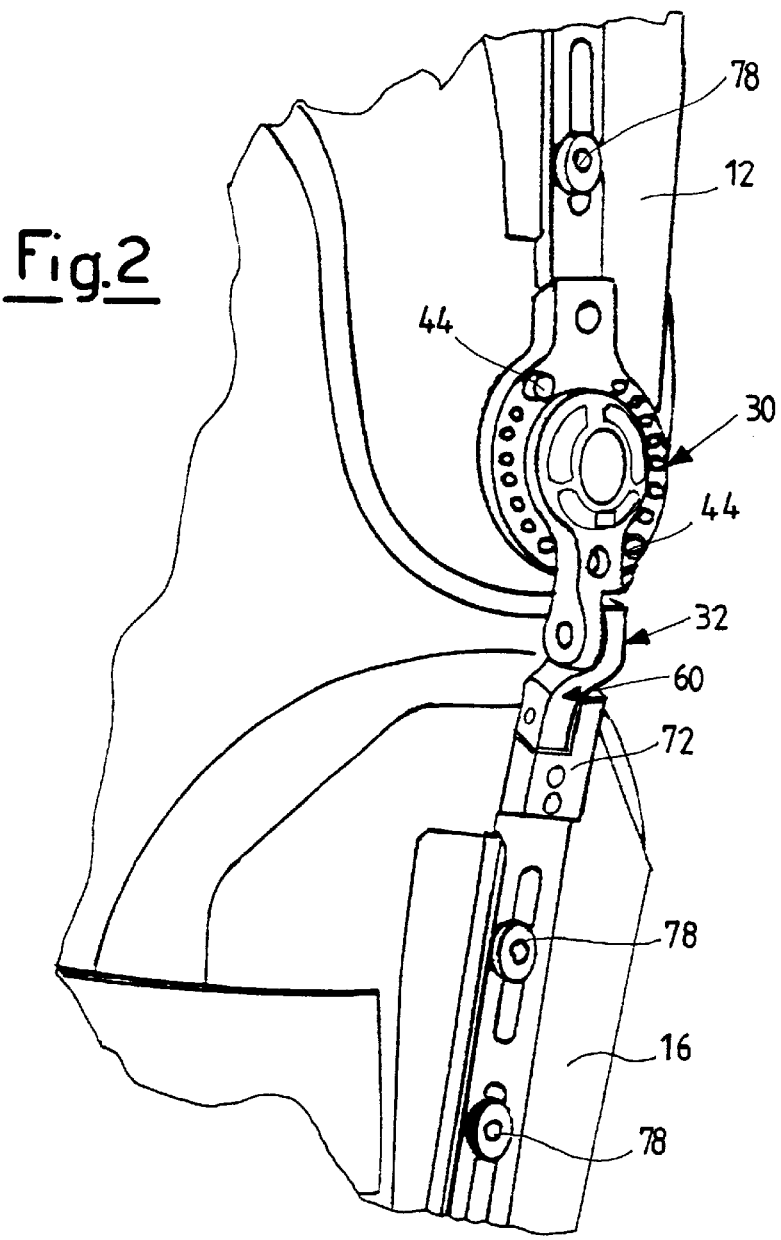
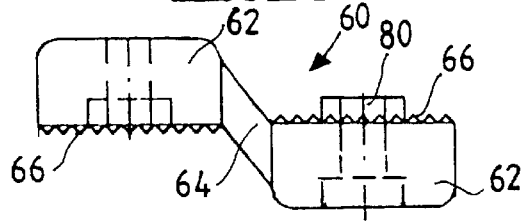

ARTICULATED ROD FOR A HIP SUPPORT

The present invention refers to an articulated rod for a hip support.

It is known that hip supports are surgical medical appliances that are used when a person has problems of hip dislocation, more in particular in the cases where the head of the femur tends to come out of its own seat in the hip. Elderly people, and in particular women, have problems of this kind, which are usually dealt with by resorting to a surgical operation for reconstruction of the head of the femur by means of a titanium prosthesis. Following upon a surgical operation of this kind, it is necessary to provide appropriate protections for the hip, at least for the period immediately following on the operation, in order to prevent the head of the femur from coming out of its seat.

For a long time now there have been available on the market hip supports that are made up of a pelvis harness, which embraces the patient's pelvis, and a thigh harness, which embraces the patient's thigh. The pelvis harness and thigh harness are connected together by means of an articulated rod which limits the patient's movements so as to prevent any movements that might prove dangerous for the patient.

A traditional articulated rod comprises a first element, designed to be connected to the pelvis harness, and a second element, designed to be connected to the thigh harness. Set between the first element and the second element is a hinge that enables mutual rotation of the two elements.

The hinge is made up of two adjacent disks, each of which is provided with a slot along its own periphery. The two disks are set one on top of the other in such a way that also the slots overlap at least partially, so as to identify an opening, the length of which is adjustable. Along its own periphery, each of the two disks is provided with teeth, between which a wedged-shaped element can be introduced, which blocks the two disks together in such a way as to form a single monolithic element provided with the opening formed by the overlapping slots of the two disks.

The first element of the articulated rod is fixed to one of the two disks, whilst a third plate provided with a pin is associated to the other disk in such a way that it can rotate. The said pin is inserted in the opening identified by the two partially overlapping slots.

The third plate ends in an extension provided with an articulation which enables the second element of the articulated rod to rotate with respect to the first element, so as to bring the former element up to or move it away from the patient's thigh and thus adapt the articulated rod to the conformation of the patient's leg.

The articulation is formed when a plane portion of the extension of the third plate, which is provided on one free surface with a toothing. The said toothing meshes with a corresponding toothing of an end portion of the second element of the articulated rod. The toothings are then blocked by means of a screw.

The traditional rod described above is used after prior setting of the length of the opening identified by the overlapping slots according to instructions given by a doctor. Setting is achieved by rotating the first plate with respect to the second plate. Subsequently, the articulation is set by adapting it to the physical structure of the patient. Next, the articulated rod can be mounted, on one side on the pelvis harness, and on the other side on the thigh harness. At this point, the hip support is'ready to be worn.

The aforesaid articulated rod for a traditional hip support is notoriously not only difficult to adjust, but regulating it is extremely laborious and only relatively precise.

In addition, when the rod is mounted on a hip support that is to be worn by a person who has some physical defect or, more simply, who is particularly fat or particularly thin, usually it assumes an inappropriate position and may cause discomfort to the patient who is wearing the hip support.

A purpose of the present invention is to eliminate the technical problems referred to above by providing an articulated rod for a hip support that can be adjusted in a simple, fast, and moreover substantially precise way.

Another purpose of the present invention is to provide an articulated rod for a hip support that is always properly positioned on the hip support, independently of the physical characteristics of the patient wearing the latter; this, in particular, in order not to induce distress or discomfort in the user.

Not the least important purpose of the present invention is to provide a an articulation rod for a hip support that is basically simple, safe, and reliable.

These and other purposes according to the present invention are achieved by providing an articulated rod for a hip support according to Claim 1.

Other characteristics of the present invention are moreover defined in the ensuing claims.

Advantageously, the articulated rod according to the present invention can be mounted on various types of hip supports, with the only limitation that the pelvis harness and thigh harness should be provided with seats suitable for receiving the said articulated rod.

Further characteristics and advantages of an articulated rod for a hip support according to the present invention will emerge more clearly evident from the ensuing description, which is provided purely to give explanatory and non-limiting examples, with reference to the attached schematic drawings, in which:

FIG. 2 shows an enlarged portion of a rod according to the invention, in a second embodiment;

FIG. 4 is an enlarged side elevation of a detail of an articulation of the rod.

Figure 1:
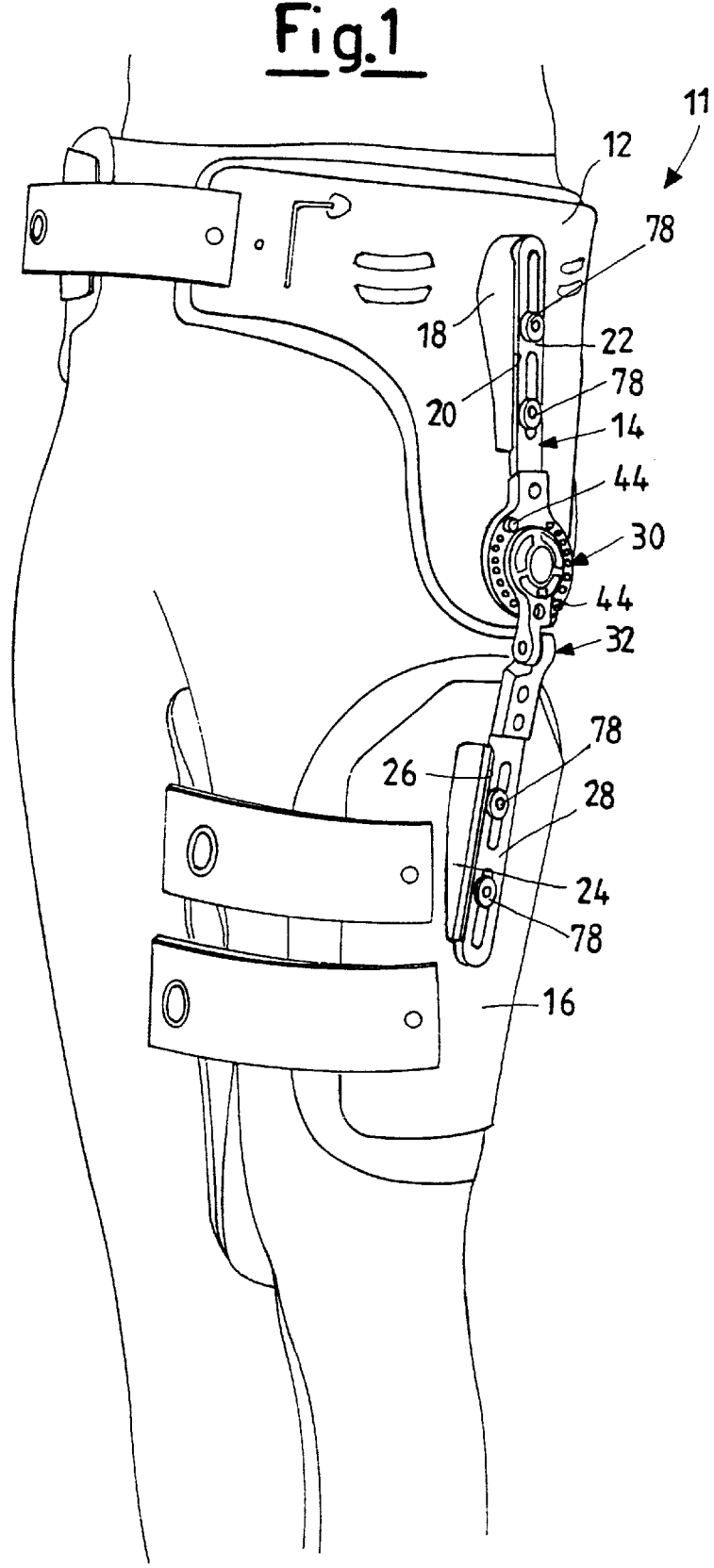
FIG. 1 shows a rod according to the invention, mounted on a hip support, in a first embodiment.
Figure 3:
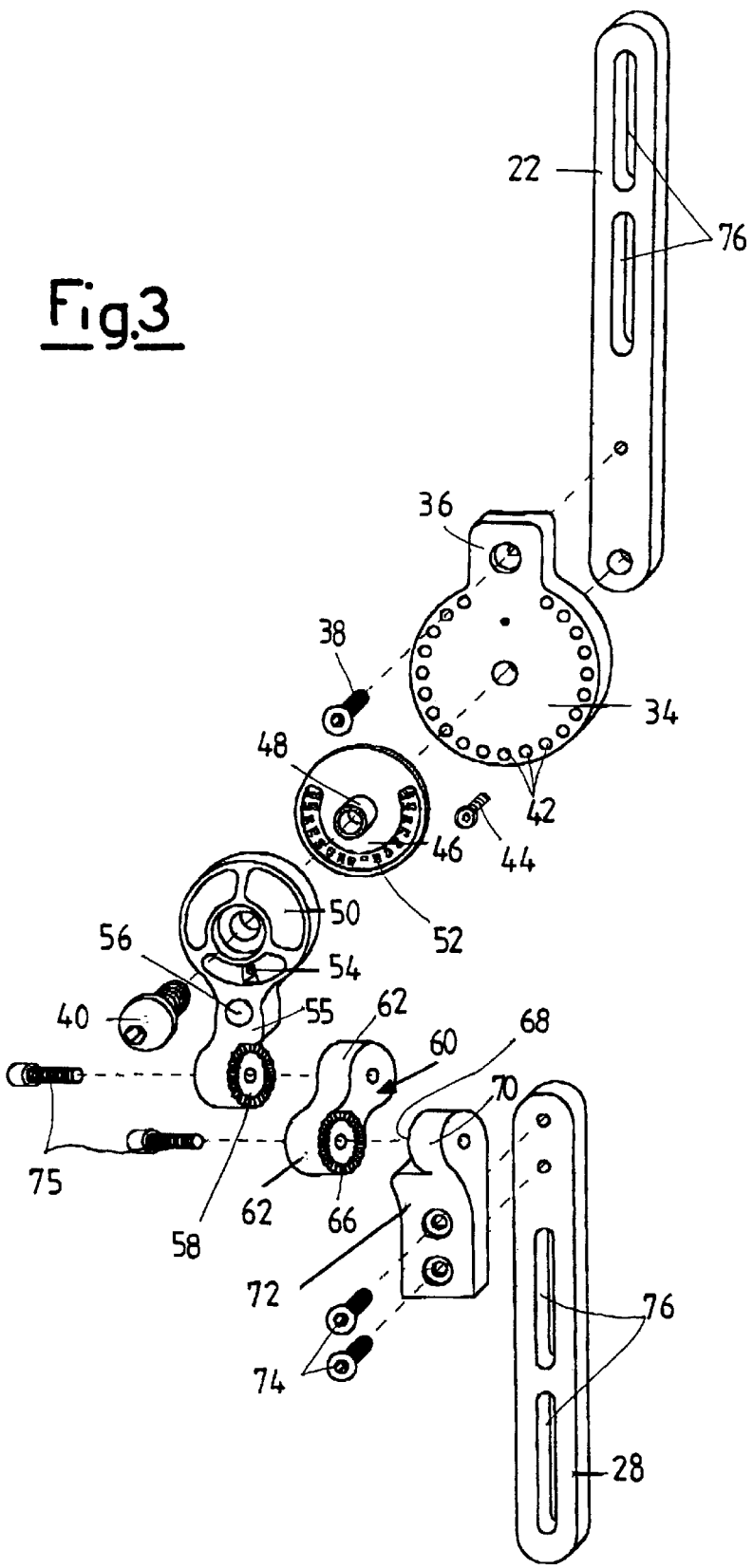
FIG. 3 is an exploded view of the rod in the second embodiment of the present invention.

With reference to the above figures, an articulated rod for a hip support is illustrated, the hip support being designated, as a whole, by the reference number 11.

The hip support 11 is made up of a pelvis harness 12 which is connected, via an articulated rod 14 according to the present invention, to a thigh harness 16.

The pelvis harness 12 has a protruding portion 18 provided with a groove 20 which identifies a seat where a first element 22 of the articulated rod 14 is to be housed.

On the opposite side, the thigh harness 16 has a protruding portion 24 similar to that of the pelvis harness 12, which is also provided with a groove 26 that identifies a seat in which a second element 28 of the articulated rod 14 is to the housed.

The first element 22 and second element 28 which make up the articulated rod 14 are joined together by means of a hinge 30 provided with an articulation 32.

The hinge 30 is obtained by means of two substantially disk-shaped plates set on top of one another.

One first plate 34 has a radial thickened portion 36 provided with a through hole in which a first screw 38 is inserted for blocking the plate 34 itself on the element 22. The plate 34 moreover has a second through hole in which a second screw 40 is inserted. The screws 38 and 40 are fixed in threaded holes of the element 22 which are aligned with the through holes of the plate 34.

The plate 34 has, along its own periphery, a series of threaded through holes 42 inside which screws or adjustment elements 44 can be inserted.

A washer 46 made of self-lubricating plastic material is set against the plate 34. The washer 46, which is disk-shaped, is provided with a central hole set in line with the central hole of the plate 34. From the edges of such a hole there extends a sleeve portion 48 that inserts in a through hole, also set at the centre, of an articulation plate 50. The washer 46 has, along its own periphery, a graduated scale 52, which is set in an area corresponding to the holes 42 but further inside in the plate 34.

The plate 50 is also disk-shaped and has a window 54 through which it is possible to read the indications of the graduated scale 52.

Inside the central holes of the plate 50, of the washer 46, and of the plate 34 is inserted the screw 40, as closing element, which blocks on the element 22 to keep the elements of the hinge 30 clamped together, and thus to keep the hinge 30 itself closed.

Integral with one end of the plate 50 is an extension 55 which is provided with a clamping hole 56 and ends with a plane portion 58 set on a plane orthogonal with respect to the plane of the plates 34 and 50, the plane portion 58 being disk-shaped and being provided with teeth along its entire perimeter. The portion 58 is connected to an articulation element 60 which enables regulation of abduction, adduction, and alignment of the pelvis harness 12 with respect to the thigh harness 16.

The element 60 structure is made up of a pair of cylindrical washers, each of which is designated by 62, which are joined together by means of an inclined intermediate portion 64. The element 60 is monolithic and is shaped in such a way that the two front surfaces 66, which are set facing opposite sides of each washer 62, are substantially contained in the same plane. These surfaces 66 are moreover provided with teeth for meshing with the portion 58 of the extension 55 on one side, and with a portion 68, provided with teeth and similar to the portions that have just been described, of an extension 70 protruding from a block 72.

The block 72 is fixed, by means of a pair of screws 74, to the second element 28 of the articulated rod 14.

The extension 55 has a through hole aligned with a through hole of one of the washers 62 for introduction therein of a screw 75 and consequent clamping of the connection. Likewise, also the other washer 62 of the articulation element 60 has a through hole aligned with a through hole of the extension 70 of the block 72, for insertion therein of another screw 75 and consequent clamping of the connection.

The elements 22 and 28 of the rod 14 are each moreover provided with a pair of slots 76 for introduction of the screws 78 for fixing the rod 14 to the pelvis harness 12 and the thigh harness 16.

Use and operation of an articulated rod for a hip support according to the present invention are described in what follows.

According to the doctor's instructions, two screws 44 are inserted in the holes 42 in such a way as to limit movement of the leg.

An explanatory and non-limiting example is provided, which is illustrated in FIGS. 1 and 2, where one first screw 44 may be seen that is set so as to prevent the patient from bending his/her leg backwards beyond a position where his/her leg is vertical and parallel to the body, whilst at the front another screw 44 is set in the end hole 42 and, consequently, does not limit the patient's movements.

Subsequently, once the patient has put on the hip support 11 and fixed the rod 14 on it, the articulation 30 is adjusted so as to adapt it to the physical conformation of the patient. This is done by means of the screws 75 that are loosened so as to rotate the element 60 and the block 62. When the appropriate position is found, the screws 75 can be tightened.

At this point, the hip support 11 is may be used and can perform its function of containment of the femur head and, at the same time, limits movement of the patient's leg. In fact, when the patient wearing the hip support 11 moves his/her leg, the hinge can turn only as far as the point where the extension 55 comes up against one of the adjustment screws 44, and further movements of the leg are prevented.

Variations and modifications to the articulated rod 14 according to the invention are of course possible. For example, as shown in FIG. 1, the rod 14 may also be used without the element 60, by meshing the portion 68 of the block 72 directly with the portion 58 of the plate 50. In addition, the plane portion 58, the portion 68, and the surfaces 66 meshed with them can be provided with male-female elements 80.

An embodiment of this sort is suitable for being used by patients having a normal physical structure, whilst the embodiment of the rod 14 with the articulation element 60 is especially suited for being used by persons who are particularly fat or particularly thin.

It has in practice been found that an articulated rod for a hip support according to the present invention is particularly advantageous not only because it can be easily and quickly adjusted in a fast, simple, and substantially precise way, but also because it is adaptable to persons having a particular physical structure, for example persons who are particularly fat or particularly thin, or who have thigh malformations. In such cases, in fact, the rod according to the present invention makes it possible to regulate the abduction and adduction movements and, moreover, to maintain the pelvis harness and thigh harness mutually aligned.

An articulated rod for a hip support thus conceived may be subject to numerous modifications and variations, all of which do not depart from the scope of the invention. In addition, all the items can be replaced by elements that are technically equivalent.

In practice the materials used, as well as the dimensions, may be any whatsoever according to the particular technical requirements.

What is claimed is:

1. An articulated rod (14) for a hip support(ll) comprising at least one first element (22) designed to be associated to a pelvis harness (12), and a second element (28) designed to be associated to a thigh harness (16), said first element (22) and second element (28) being joined together by means of a hinge (30), characterized in that said hinge (30) comprises at least one first plate (34) which is fixed to a first element (22) and has a face set at least against a corresponding face of an articulation plate (50), and between a first plate (34) and an articulation plate (50) a washer (46) made of self lubricating material is set and said first plate (34) and said articulation plate (50) being joined by means of a closing element (40) inserted in aligned through holes of said first plate (34) and of said articulation plate (50), said first plate (34) moreover having a plurality of holes (42) which are set along at least one portion of its own periphery and in which adjustment elements (44) can be inserted, said adjustment elements (44) being designed to limit rotation of said articulation plate (50) with respect to said first plate (34).

2. An articulated rod (14) according to claim 1, characterized in that a washer (46) between a first plate (34) and an articulation plate (50), is provided with a central through hole aligned with a central hole of said first plate (34) and of said articulation plate (50), and extending from said through hole a sleeve-shaped portion (48) which inserts in a central hole of a first plate (34) and a central hole of an articulation plate (50).

3. An articulated rod (14) according to claim 2, characterized in that said washer (46) has, along at least one portion of its periphery, at least one graduated scale (52) which is set in an area corresponding to a plurality of adjustment element holes (42) on said first plate (34).

4. An articulated rod (14) according to claim 3, characterized by an articulation plate (50) has at least a window (54) through which the indications of said graduated scale (52) can be read.

5. An articulated rod (14) according to claim 4, characterized by said articulation plate(50) comprises a radial extension (55) which is integral with said articulation plate (50) and ends with a plain portion(58) lying on a plane that is orthogonal to the plane of said first plate (34) and said articulation plate (50), and being provided with teeth along its entire perimeter, said plane portion(58) being meshed with at least one articulation element (60) consisting of a pair of washers (62) which are joined together by means of an intermediate portion (64), front surfaces (66) which are set facing opposite sides of each of said washers (62) being substantially contained in the same plane and being provided with teeth (66) for meshing with said plane portion (58) of said radial extension (55) on one side, and with a portion (68), provided with teeth, of an extension (70) which also contains two through holes for the introduction therein of screws (74) for fastening to said second element (28) of said articulated rod (14).

6. An articulated rod (14) according to claim 5, characterized in that said radial extension (55) has at least one through hole aligned with a through hole of a first washer (62) of said articulation element (60) for introduction therein of a screw (75) and for fastening said radial extension to said articulation element (60).

7. An articulated rod (14) according to claim 5, characterized in that one second washer (62) of said articulation element (60) has a through hole aligned with a through hole of an extension (70) fixed to a second element (28) of said articulated rod (14), for introduction therein of another screw (75) and for fastening said articulation element to said extension (70).

8. An articulated rod (14) according to claim 5, characterized in that a plane portion (58) of said radial extension (55) being equipped with a male element (80), a plane portion (68) of extension (70) fixed to said second element (28) of said articulated rod (14), being equipped with a female element (80') and said surfaces (66) of said washers (62) comprising said articulation element (60), meshed with them are provided with male-female elements (80, 80') respectively.

\* \* \* \* \*